(12) United States Patent
Gamber et al.

(10) Patent No.: US 8,656,917 B2
(45) Date of Patent: Feb. 25, 2014

(54) LIMB SUPPORT DEVICE

(75) Inventors: Michael R. Gamber, Conroe, TX (US); Glen Hotchkiss, Montgomery, TX (US); Stephen F. Tester, II, Spring, TX (US)

(73) Assignee: Gemm Quality Products LLC, Conroe, TX (US)

( * ) Notice: Subject to any disclaimer, the term of this patent is extended or adjusted under 35 U.S.C. 154(b) by 754 days.

(21) Appl. No.: 12/628,101

(22) Filed: Nov. 30, 2009

(65) Prior Publication Data

US 2011/0126843 A1 Jun. 2, 2011

(51) Int. Cl.
  *A61G 15/00* (2006.01)
(52) U.S. Cl.
  USPC ............. 128/845; 5/620; 5/621; 5/623; 5/624
(58) Field of Classification Search
  USPC ........... 128/845; 297/195.11, 183.16; 403/61; 5/620–621, 623–624
  See application file for complete search history.

(56) References Cited

U.S. PATENT DOCUMENTS

| | | | |
|---|---|---|---|
| 2,685,286 A * | 8/1954 | Torricelli | 600/553 |
| 2,732,269 A | 1/1956 | Astroff | |
| 2,873,987 A * | 2/1959 | Larson | 403/61 |
| 3,696,826 A | 10/1972 | Gruzalski | |
| 5,000,168 A | 3/1991 | Lipson | |
| 5,035,094 A * | 7/1991 | Legare | 52/118 |
| 6,026,812 A | 2/2000 | Lipson | |
| 6,712,781 B1 | 3/2004 | Sheppard | |
| 7,055,524 B1 * | 6/2006 | Taimoorazy | 128/845 |
| 2003/0034037 A1 * | 2/2003 | Klemm | 128/845 |
| 2006/0237947 A1 * | 10/2006 | Michelau et al. | 280/293 |
| 2007/0225135 A1 * | 9/2007 | Webber | 482/140 |
| 2008/0150331 A1 * | 6/2008 | Chen | 297/195.11 |
| 2008/0222936 A1 * | 9/2008 | Moody et al. | 42/73 |

* cited by examiner

*Primary Examiner* — Patricia Bianco
*Assistant Examiner* — Caitlin Carreiro
(74) *Attorney, Agent, or Firm* — Law Offices of Mark L. Berrier

(57) ABSTRACT

A limb support device that includes a vertical support, a base connected to a lower end of the vertical support and a head portion connected to an upper end of the vertical support. The base includes a set of foldable legs that can be positioned upward, where each leg is substantially parallel to the vertical support, or downward, where each leg is substantially perpendicular to the vertical support so that the vertical support is held upright. The head portion has a generally concave saddle that can hold a limb above the vertical support. The saddle can be pivoted so that it can be positioned at a variable angle with respect to the vertical support. The vertical support itself is adjustable in length.

5 Claims, 5 Drawing Sheets

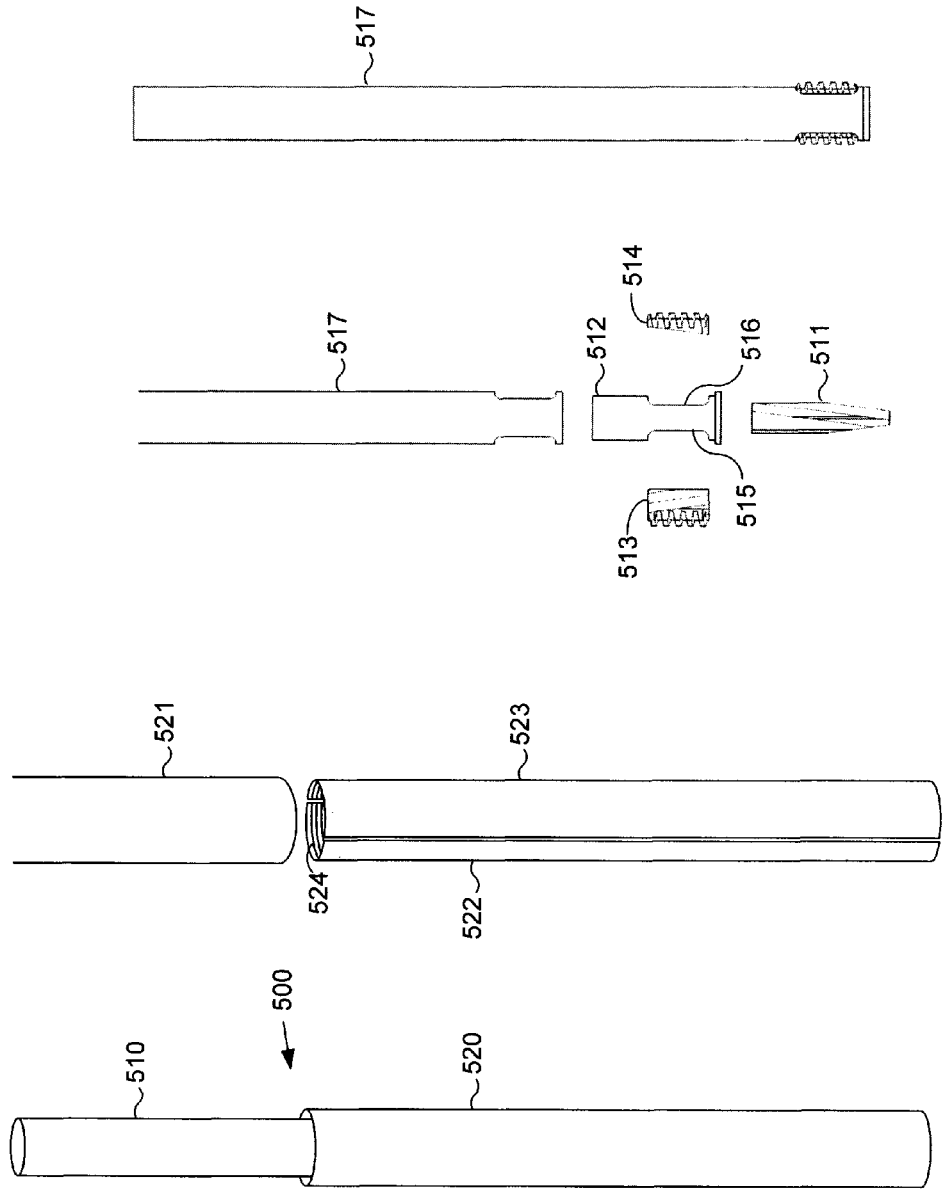

LIMB SUPPORT DEVICE

BACKGROUND

1. Field of the Invention

The invention relates generally to medical devices, and more particularly to devices that are designed to provide support to a person's limb when it is necessary to elevate the limb for purposes of medical treatment.

2. Related Art

It is sometimes helpful in the treatment of medical conditions to elevate a person's limb (e.g., an arm or a leg). For instance, a person may suffer a broken bone or may have surgery that involves one of his limbs. It may aid in the person's recovery to elevate the affected limb in order to reduce the blood pressure in the limb or to improve circulation in the limb. There is also an increasing percentage of the population that suffers from circulatory conditions that are treated in large part by elevating the limbs whenever possible.

A number of specialized devices are available in medical treatment facilities to elevate a person's limbs. There are far fewer devices that are available outside medical treatment facilities. If a person is at home, he will typically elevate his arm or leg by positioning it on top of whatever is available. For example, when sitting in a chair, there may be an ottoman on which the leg can be rested. Alternatively, the leg can be placed on a coffee table or another chair, or the person can rest his leg on a couch.

Various specialized devices have been proposed for allowing a person to elevate an arm or leg. For instance, U.S. Pat. Nos. 5,000,168 and 6,026,812 to Lipson disclose supports that can be used for arms or legs. These supports have various means for adjusting the height and angle at which the limb is supported, but the devices are very bulky and not easily transportable.

U.S. Pat. No. 3,696,826 to Gruzalski discloses a leg supporting device that is designed to be attached to a leg cast, and can be swiveled from a first position in which it is essentially parallel to the cast to a second position in which it extends perpendicular to the cast, allowing the cast to be supported above the floor. While this device is relatively easy to transport when the user is outside the home, it has very little adjustability as to the height at which the cast is supported, and is not conveniently used with an arm cast. Further, this device is not suitable for supporting a limb that is not in cast. U.S. Pat. No. 6,712,781 to Sheppard discloses a leg support similar to that of Gruzalski. This device is strapped to a leg or leg cast, and a telescoping support can be moved between positions that are perpendicular and parallel to the leg.

U.S. Pat. No. 2,732,269 to Astroff discloses an arm and leg support device that has a pivoting, U-shaped brace for supporting the arm or leg, an adjustable telescopic leg, and a folding base. Although this device can be folded, it is still rather bulky, and not particularly convenient to transport. Further, the U-shaped brace has little adjustability, and the height adjustment, which uses a thumbscrew to hold one piece of the telescoping leg inside the other, is not very secure.

Despite the fact that elevation of limbs is widely recommended, and even prescribed, for the treatment of various medical conditions, few of the devices described above are commonly used. This may be the result of many different factors, such as the cost of these devices, the inconvenience of using the devices because of their weight and/or bulkiness and the limited adjustability of the devices. There is therefore still a need for a lightweight, low-cost limb support for both arms and legs that is conveniently transportable and highly adjustable.

SUMMARY OF THE INVENTION

This disclosure is directed to support devices that are designed to provide support to a person's limb when it is necessary to elevate the limb for purposes of medical treatment.

In one particular embodiment, a limb support device includes a vertical support, a base connected to a lower end of the vertical support and a head portion connected to an upper end of the vertical support. In this embodiment, the base includes a set of foldable legs that can be positioned upward, where each leg is substantially parallel to the vertical support, or downward, where each leg is substantially perpendicular to the vertical support so that the vertical support is held upright. The head portion has a generally concave saddle that can hold a limb above the vertical support. The saddle can be pivoted so that it can be positioned at a variable angle with respect to the vertical support. The vertical support itself is adjustable in length.

In one embodiment, the limb support device is continuously variable to enable maximum comfort in supporting a person's limb. For example, the saddle may be coupled to the vertical support by a ball-and-socket type connection that allows the saddle to be pivoted to achieve the best orientation. The vertical support may use threaded, telescoping tubes to allow continuously variable length adjustment. In one embodiment, the threads of the tubes can be disengaged to allow the tubes to be moved more quickly than rotating the tubes with respect to each other. In one embodiment, the base includes a locking mechanism to allow the legs to be easily folded upward for storage or transport, or locked down for use. This embodiment may use a spring mechanism to urge the legs upward when they are not locked down. A guide pin on each leg can be positioned in a locking indentation to lock the leg in the downward position for use.

Numerous other embodiments are also possible.

BRIEF DESCRIPTION OF THE DRAWINGS

Other objects and advantages of the invention may become apparent upon reading the following detailed description and upon reference to the accompanying drawings.

FIGS. 5A-5D are diagrams illustrating various views of a vertical support assembly in accordance with one embodiment.

Figure 1:
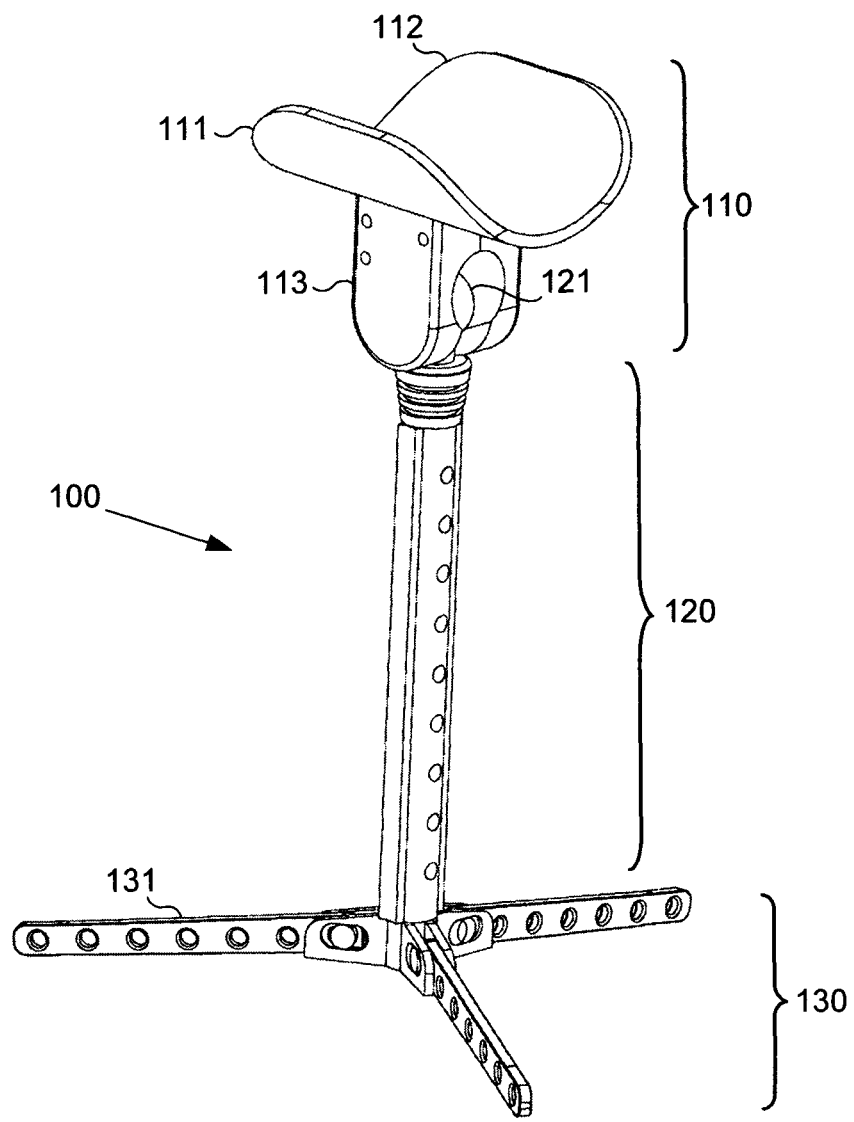
FIG. 1 is a diagram illustrating a perspective view of a limb support in accordance with one embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims.

DETAILED DESCRIPTION OF PREFERRED EMBODIMENTS

One or more embodiments of the invention are described below. It should be noted that these and any other embodiments described below are exemplary and are intended to be illustrative of the invention rather than limiting.

Figure 3:
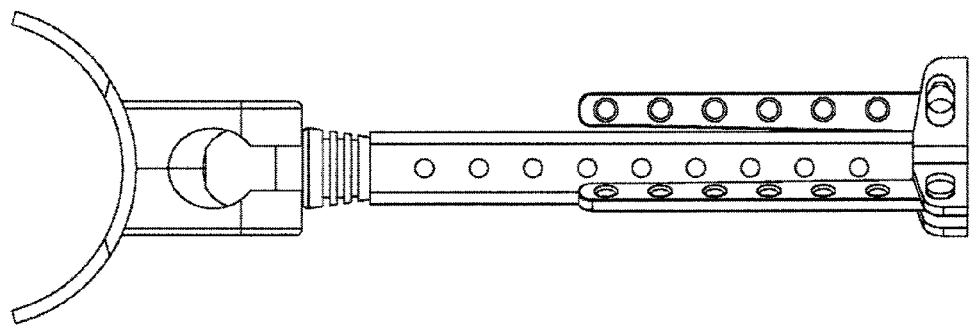
FIG. 3 is a diagram illustrating a front view of a limb support in accordance with one embodiment.
Figure 2:
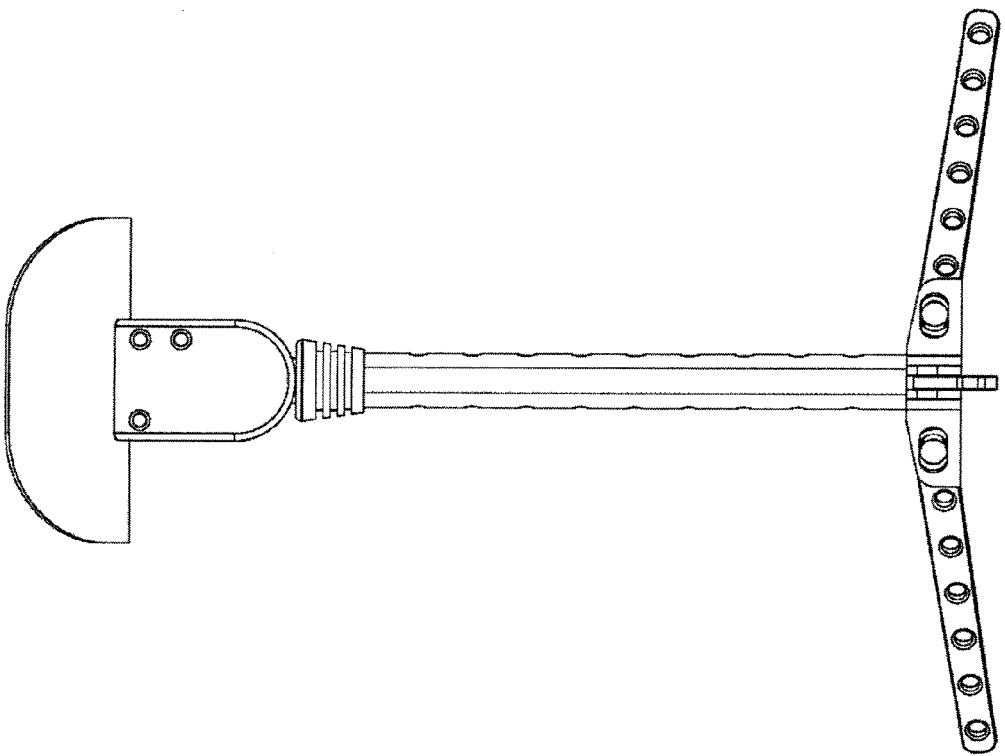
FIG. 2 is a diagram illustrating a side view of a limb support in accordance with one embodiment.

Referring to FIGS. 1-3, several views of a limb support in accordance with one embodiment are shown. FIG. 1 is a perspective view of the limb support, FIG. 2 is a side view and FIG. 3 is a front view. It should be noted that this embodiment of the limb support has folding legs, and the legs are in a first, extended position in FIGS. 1 and 2, while the legs are in a second, folded position in FIG. 3.

In the embodiment of FIGS. 1-3, limb support 100 includes a head portion 110, a vertical support 120 and a base 130. Head portion 110 includes a saddle 111 that is curved upward in a concave or "U" shape. That curved shape of the saddle provides a stable place for a person to rest his or her arm or leg. That curved shape also conforms somewhat to the shape of the limb to distribute the pressure between the limb and the saddle over a larger area. A cushioning material 112 is attached to the upper, concave portion of the saddle in this embodiment to provide additional comfort. The cushioning material may comprise any suitable material, and may be perforated, textured or otherwise designed to enhance the breathability and comfort of the support.

Saddle 111 is connected in this embodiment to the socket portion 113 of a ball-and-socket joint. The ball portion 121 of the ball-and-socket joint is connected to the upper end of vertical support 120. Ball portion 121 fits within socket portion 113 and is held in place within the socket by friction. Socket portion 113 may include screws or other means to tighten or loosen the socket over ball portion 121 and thereby adjust the amount of friction between the ball portion and the socket portion. The ball-and-socket joint allows the orientation of saddle 111 to be adjusted with respect to vertical support 120. The use of a ball-and-socket joint allows the saddle orientation to be continuously adjusted, rather than having a limited number of discrete positions. The ball-and-socket joint also enables adjustment with a minimum amount of effort, as the saddle can simply be moved to the appropriate orientation. At most, the ball-and-socket joint may need to be tightened or listened to adjust the friction between the ball portion and the socket portion.

In this embodiment, vertical support 120 includes two tubular structures that are concentrically positioned to provide a telescoping support. A locking mechanism within vertical support 120 can be released to allow the relative positions of the tubular structures (hence the length of the vertical support) to be adjusted. When vertical support 120 has been ingested to the proper length (height), the locking mechanism is engaged to prevent relative movement between the two tubular structures.

The lower end of vertical support 120 is connected to a base 130. Base 130 is designed to have two positions. In a first position (illustrated in FIG. 1), a set of legs (e.g., 131) extend outward, generally perpendicular to vertical support 120. With the legs in the first position, limb support 100 can be placed on a flat surface such as a floor or table, and base 130 will hold vertical support 120 upright so that a person's limb can be placed on saddle 111, where it will be held in a stable, elevated position. The legs of base 130 can alternatively be placed in a second position, which is used to store or transport limb support 100. In the second position, each of the legs is pivoted upward so that it is substantially parallel to vertical support 120. The second position is illustrated in FIG. 3.

Figure 4C:
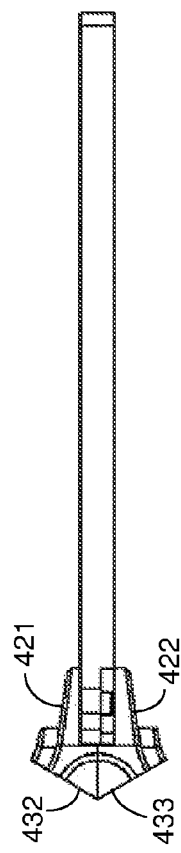
FIGS. 4A-4D are diagrams illustrating various views of a leg assembly in accordance with one embodiment.
Figure 4D:
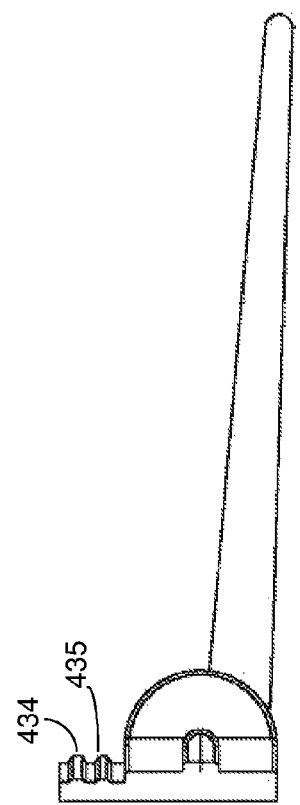
Figure 4A:
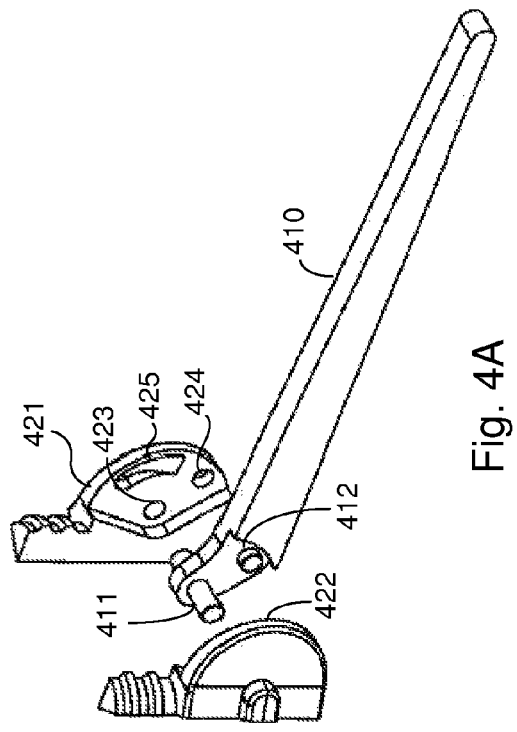
Figure 4B:
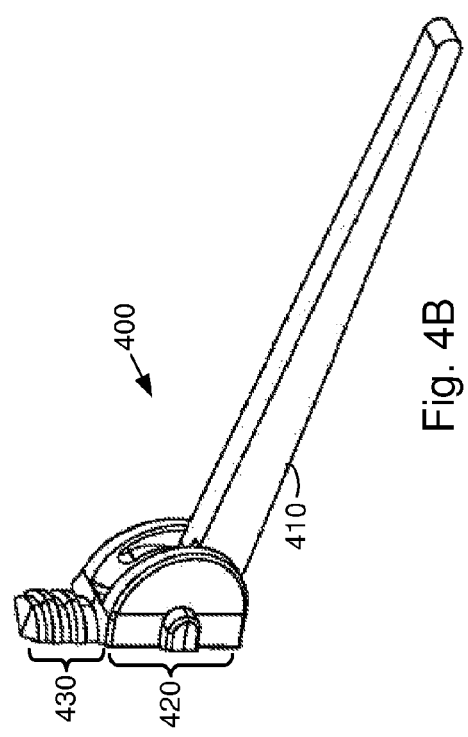

In one embodiment, base 130 consists of three identical leg assemblies that are coupled together to form the base. An exemplary leg assembly is illustrated in detail in FIGS. 4A-4D. FIG. 4A is a perspective view of a leg assembly 400. The assembly includes a leg 410, a pivot mechanism 420 and an attachment portion 430. Leg 410 is an elongated, rigid structure that extends outward from pivot mechanism 420. Leg 410 may be solid, or the weight of the leg may be reduced, for example, by making it hollow or forming holes through it (as shown in FIGS. 1-3). Leg 410 extends with respect to the housing of pivot mechanism 420 and attachment portion 430. When leg 410 is in a first, extended position as shown in FIGS. 4A-4D, the leg locks into position so that it cannot freely pivot out of this position. When a user releases the locking mechanism, leg 410 pivots upward toward attachment portion 430. The pivoting and locking mechanisms will be described in more detail below.

Attachment portion 430 has a curved surface 431 that faces leg 410 and two flat surfaces 432-433. Surfaces 432 and 433 are at an angle of 120° from each other. Curved surface 431 is a generally cylindrical surface. Thus, when three of the leg assemblies are placed with their flat surfaces (e.g., 432, 433) together, the attachment portions (e.g., 430) form a generally cylindrical shape that can be positioned within the lower end of the vertical support tube. Attachment portion 430 is sized so that the cylindrical shape of the attachment portions of the three leg assemblies are friction fit within the vertical support tube and are held together by the vertical support tube. It should be noted that the embodiment illustrated in FIGS. 4A-4D includes a pair of ridges (434, 435) that are designed to interlock with complementary ridges on the interior of the lower end of the vertical support tube. This securely connects the three leg assemblies to the vertical support tube.

Attachment portion 430 is formed in this embodiment by two housing pieces (421, 422) that also serve as a housing for pivot mechanism 420. Each of housing pieces 421 and 422 has a first indentation (e.g., 423) that receives a pivot pin 411 that extends through the end of leg 410. Consequently, leg 410 can pivot about pin 411 within the housing of pivot mechanism 420. The first indentations in housing pieces 421 and 422 that receive pivot pin 411 are sufficiently deep to allow some movement of leg 410 between the two housing pieces without allowing pivot pin 411 to come out of the first indentations. A spring (not shown in the figures) is positioned between leg 410 and housing piece 422 in order to urge the leg toward housing piece 421.

Leg 410 includes a guide pin 412 which extends through the end of leg 410 near pivot pin 411. Guide pin 412 extends from leg 410 toward housing piece 421. The interior of housing piece 421 includes a second indentation 424, as well as a groove 425, each of which can receive guide pin 412. When leg 410 is in the first, extended position (roughly perpendicular to the vertical support tube), guide pin 412 extends into second indentation 424, thereby locking the leg into position. As noted above, the spring positioned between leg 410 and housing piece 422 urges leg 410, as well as guide pin 412 toward housing piece 421, so that the guide pin falls into second indentation 424, locking the leg into the extended position. A user can move leg 410 toward housing piece 422 (away from housing piece 421) to move guide pin 412 out of second indentation 424, thereby allowing the leg to pivot upward. As leg 410 is pivoted upward, guide pin 412 is urged into groove 425. Groove 425 is more shallow at the lower end and deeper at the upper end. As a result, as the spring urges guide pin 412 deeper into groove 425, leg 410 is urged upward toward the folded position. Because groove is tapered in this manner, leg 410 can be moved from the upward, folded position to the downward, extended position without first having to move the leg away from housing piece 421 -- the leg will be moved away from the housing piece as it is pivoted downward.

Referring to FIGS. 5A-5C, an exemplary structure of the vertical support portion of the limb support device is shown in more detail. FIG. 5A shows that vertical support 500 includes an inner tubular structure 510 and an outer tubular structure 520. Inner tubular structure 510 fits within outer tubular structure 520 to form a telescoping vertical support. In one embodiment, inner tubular structure 510 is locked in position within outer tubular structure 520 using a locking mechanism that causes a set of outward-facing threads on the inner tubular structure to engage a set of inward-facing threads on the outer tubular structure. The threads on the inner tubular structure can be moved radially inward to disengage the threads of the outer tubular structure, thereby allowing the inner tubular structure to be repositioned (extended or retracted).

Referring to FIG. 5B, the components of outer tubular structure 520 are shown. In this embodiment, the outer tubular structure includes an outer sleeve 521 and a pair of inserts 522 and 523. Inserts 522 and 523 are sized to fit tightly within outer sleeve 521. Tubular structure 520 is constructed by placing semi-cylindrical inserts 522 and 523 together and pressing them into outer sleeve 521. Each of inserts 522 and 523 has a set of inward-facing threads (e.g., 524) that can be engaged by the inward-facing threads of inner tubular structure 510.

Referring to FIG. 5C, the components of inner tubular structure 510 are shown. In this embodiment, a pair of locking blocks 513 and 514 are positioned in carrier 512. Each of locking blocks 513 and 514 has outward-facing threads and can move radially inward or outward from the central axis of carrier 512 to engage the inward-facing threads of outer tubular structure 520. Each of locking blocks 513 and 514 has grooves on the back (the portion on the opposite side of the threads) which engage structures on an engagement wedge 511. Engagement wedge 511 can move axially (up and down in the figure) within carrier 512. Because locking blocks 513 and 514 are constrained to fit within openings 515 and 516 in carrier 512, they move radially inward or outward as engagement wedge 511 moves axially up or down within the carrier. The assembly of carrier 512, engagement wedge 511 and locking blocks 513 and 514 is inserted in guide sleeve 517 to form the inner tubular structure of the vertical support.

It should be noted that a spring is positioned between the top end of carrier 512 and engagement wedge 511 to urge the engagement wedge downward. This, in turn, urges locking blocks 513 and 514 radially outward so that they will engage the threads of the outer tubular structure. A cable is connected to the top of engagement wedge 511 to allow the engagement wedge to be pulled upward, thereby causing locking blocks 513 and 514 to move radially inward, disengaging the threads of the outer tubular structure. This allows the inner tubular structure to be moved within the outer tubular structure.

Figure 6:
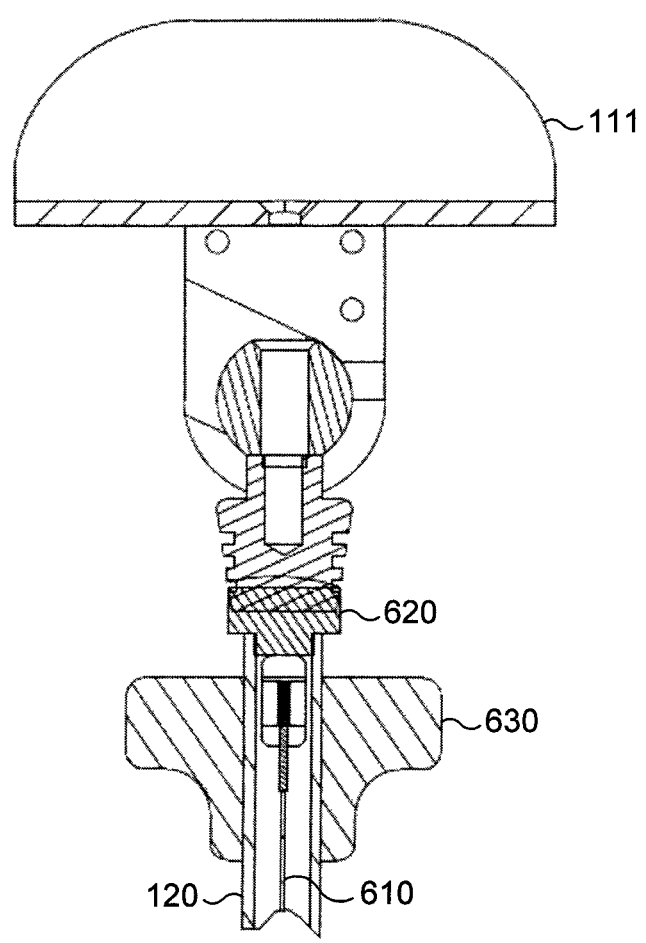
FIG. 6 is a diagram illustrating the connection between vertical support and head portions of a limb support device in accordance with one embodiment.

As shown in FIG. 6, cable 610 extends from top of the engagement wedge to the bottom of a coupling assembly 620. Coupling assembly 620 couples the ball-and-socket joint that supports saddle 111 to the vertical support 120. When coupling assembly 620 is pulled upward with respect to vertical support 120, cable 610 is also pulled upward. This pulls the engagement wedge upward and allows the locking blocks to move inward, disengaging the threads of the outer tubular structure, and allowing the inner tubular structure to be moved within the outer tubular structure. As depicted in FIG. 6, a release collar 630 is provided at the top of inner tubular structure 120 to enable a user to firmly hold this structure while pulling upward on coupling assembly 620.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein and recited within the following claims.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A limb support device comprising:
a vertical support; a base connected to a lower end of the vertical support; and
a head portion connected to an upper end of the vertical support; wherein the base includes at least three foldable legs which can be positioned in either a first position in which each of the at least three foldable legs extends in a perpendicular direction from a longitudinal axis of the vertical support or a second position in which each of the at least three foldable legs extends parallel to the longitudinal axis of the vertical support; wherein the head portion includes a upward-facing concave saddle, and wherein the head portion is pivotally connected to the vertical support and is thereby capable of being positioned at a variable angle with respect to the longitudinal axis of the vertical support; and wherein the vertical support has a length which is continuously variable, wherein the vertical support has a sleeve member that includes internal helical threads and an inner member that includes external helical threads, wherein the external helical threads of the inner member engage the internal helical threads of the sleeve member to secure the inner member in position within the sleeve member, wherein the inner member comprises a pair of locking blocks having outward-facing threads to facilitate engagement with the internal helical threads of the sleeve member, wherein the pair of locking blocks are positioned within a carrier and move radially inward or outward through openings on opposite sides of the carrier to alternately engage with and disengage from the internal helical threads of the sleeve member.

2. The limb support device of claim 1, wherein each of the pair of locking blocks further comprise grooves on a side opposite to the outward-facing threads, wherein said grooves are configured for engagement with an engagement wedge that is longitudinally movable with respect to the longitudinal axis of the vertical support, thereby causing the pair of locking blocks to move radially inward and outward and alternately engage with and disengage from the internal helical threads of the sleeve member.

3. A limb support device comprising:
   a vertical support; a base connected to a lower end of the vertical support; and
   a head portion connected to an upper end of the vertical support; wherein the head portion includes a upward-facing concave saddle, and wherein the head portion is pivotally connected to the vertical support and is thereby capable of being positioned at a variable angle with respect to the longitudinal axis of the vertical support; and wherein the vertical support has a length which is variable, and wherein the base includes at least three foldable legs which can be positioned in either a first position in which each of the at least three foldable legs extends in a perpendicular direction from a longitudinal axis of the vertical support or a second position in which each of the at least three foldable legs extends parallel to the longitudinal axis of the vertical support; wherein the base includes a locking mechanism configured to releasably secure each of the at least three foldable legs in the first position and a spring mechanism configured to urge each of the at least three foldable legs toward the second position when each of the at least three foldable legs are released from the first position, wherein the locking mechanism and spring mechanism comprise a plurality of leg housings, wherein each of the at least three foldable legs is pivotally secured within a corresponding one of the plurality of leg housings, wherein each of the plurality of leg housings includes a locking indentation spaced apart from a groove, wherein the groove has an upper end, a lower end, and a tapered depth such that the groove is more shallow at the lower end and deeper at the upper end, wherein each of the at least three foldable legs includes a guide pin that extends alternately into either the locking indentation or the groove of the corresponding one of the plurality of leg housings, wherein each guide pin includes a spring configured to urge the guide pin into either the locking indentation or the groove, wherein when the guide pin is in the groove, the guide pin is urged deeper in the groove at the upper end of the groove, thereby urging a corresponding one of the at least three foldable legs towards the second position.

4. The limb support device of claim 1, wherein the pair of locking blocks are radially movable with respect to the longitudinal axis of the vertical support, thereby alternately engaging with and disengaging from the internal threads of the sleeve member when the inner member is positioned within the sleeve member.

5. The limb support device of claim 3, wherein each leg housing includes the locking indentation and the groove on an interior of the housing.

* * * * *